(12) United States Patent
Enomoto

(10) Patent No.: US 6,413,210 B1
(45) Date of Patent: Jul. 2, 2002

(54) LIFE SPAN METER SYSTEM FOR LIGHT-SOURCE USED IN ELECTRONIC ENDOSCOPE

(75) Inventor: Takayuki Enomoto, Saitama (JP)

(73) Assignee: Asahi Kogaku Kogyo Kabushiki Kaisha, Tokyo (JP)

(*) Notice: Subject to any disclaimer, the term of this patent is extended or adjusted under 35 U.S.C. 154(b) by 0 days.

(21) Appl. No.: 09/271,456

(22) Filed: Mar. 18, 1999

(30) Foreign Application Priority Data

Mar. 19, 1998 (JP) .......................................... 10-090815

(51) Int. Cl.⁷ .................................................. A61B 1/06
(52) U.S. Cl. ...................................... 600/178; 362/574
(58) Field of Search ................................ 600/178–181; 315/129, 133, 136; 362/572, 574

(56) References Cited

U.S. PATENT DOCUMENTS 3,641,332 A * 2/1972 Reick et al. ................. 362/572
5,196,884 A * 3/1993 Sugiyama et al. ........... 355/200
5,274,611 A * 12/1993 Donohoe ...................... 368/10
5,830,121 A   11/1998 Enomoto et al.

* cited by examiner

Primary Examiner—John Mulcahy
(74) Attorney, Agent, or Firm—Greenblum & Bernstein, P.L.C.

(57) ABSTRACT

In a life span meter system for a lamp, such as a xenon lamp, used in an electronic endoscope, a counter numerically estimates a lit-time of the lamp as a numerical data whenever the lamp is turned ON. A memory stores the numerical data as a total numerical data of the lit-time of the lamp whenever the lamp is turned OFF. A determiner determines whether the total numerical data reaches a numerical life-span data which is numerically estimated from a life span of the lamp. An indicator indicates that the lamp should be exchanged with a new lamp when it is determined by the determiner that the total numerical lit-time data exceeds the numerical life-span data.

10 Claims, 12 Drawing Sheets

LIFE SPAN METER SYSTEM FOR LIGHT-SOURCE USED IN ELECTRONIC ENDOSCOPE

BACKGROUND OF THE INVENTION

1. Field of the Invention

The present invention relates to a life span meter system for a light source used in an electronic endoscope.

2. Description of the Related Art

As is well known, an electronic endoscope comprises a flexible conduit and a video-signal processing unit to which the flexible conduit is detachably joined at its proximal end. The flexible conduit includes an objective lens system provided at the distal end thereof, and a solid image sensor, such as a CCD (charge-coupled device) image sensor, associated therewith. The flexible conduit also includes an optical light guide extended therethrough and formed as a bundle of optical fibers, and the optical light guide terminates at a light-emitting end face at the distal end of the flexible conduit.

Further, the video-signal processing unit includes a light source, such as a xenon lamp, a halogen lamp or the like. When the flexible conduit is joined to the video-signal processing unit, the proximal end of the optical light guide is optically connected to the light source. Thus, an object to be photographed is illuminated by light rays emitted from the distal end of the optical light guide of the flexible conduit, and is focused on a light-receiving surface of the CCD image sensor.

The focused optical image is converted into a series of analog image-pixel signals by the CCD image sensor 14, and the series of analog image-pixel signals are fed to the video-signal processing unit in which the image-pixel signals are processed so as to produce a video signal. Then, the video signal is fed to a monitor, and then the photographed image is reproduced on the monitor on the basis of the video signal.

In general, the light source, such as the xenon lamp, the halogen lamp or the like is a consumption article, and thus must be periodically exchanged with a new one as the lamp in use gradually deteriorates. However, it is difficult to timely know an optimal point when the lamp should be exchanged with a new one. Thus, the video-signal processing un it is provided with a lamp life span meter, so that a remaining life span of the lamp is indicated by a mercury column. Consequently, it is possible to know the optimum point at which the lamp in use should be with the new lamp.

Nevertheless, the utilization of the life span meter is prohibited due to the occurrence of environmental pollution from the mercury used in the life span meter when the video-signal processing unit is treated as industrial waste.

Also, conventionally, for reproduction of a photographed image as a color image, for example, an RGB field sequential type color imaging system is utilized in the electronic endoscope. In this case, it is necessary to periodically perform an adjustment of a white-balance over the span of a life of the lamp, before the color image can be reproduced with a high quality color balance. Nevertheless, there is little likelihood that the life span meter is watched by an operator or doctor to timely know when the adjustment of the white-balance should be performed, because the life span meter is frequently attached at a location of the video-signal processing unit, which is not conveniently observable by the operator or doctor. For example, the life span meter is frequently located on a rear side of a housing of the video-signal processing unit.

SUMMARY OF THE INVENTION

Therefore, an object of the present invention is to provide a life span meter system for a light source used in an electronic endoscope that will not cause environmental pollution on disposal.

Another object of the present invention is to provide a life span meter system as mentioned above, in which it is possible to timely and surely announce a point at which the light source in use should be with a new light source.

Yet another object of the present invention is to provide a life span meter system as mentioned above, in which it is possible to timely and surely announce a point at which the light source in use should be with a new light source, and also a point at which an adjustment of a white-balance should be performed.

In accordance with the present invention, there is provided a life span meter system for a light source used in an electronic endoscope, comprising a counter that numerically determined a lit-time of the light source as a numerical lit-time data when the light source is turned ON, a memory that stores the numerical lit-time data as a total numerical lit-time data of the lit-time of the light source when the light source is turned OFF, a determiner that determines whether the total numerical lit-time data reaches a numerical life span data numerically determined from an expected life span of the light source, and an indicator that indicates the light source should be exchanged with a new light source when it is determined by the determiner that the total numerical lit-time data exceeds the numerical life span data.

Preferably, the counter comprises a subtraction-counter initially setting the numerical life span data to an initial value, and subtracting the numerical lit-time data from the initial value. In this case, the initial value of the subtraction-counter, from which the numerical lit-time data is subtracted, is stored in the memory, and the determiner determines whether the initial value of the subtraction-counter, from which the numerical lit-time data is subtracted, is less than zero, and the indicator indicates that the light source should be exchanged with the new light source when it is determined by the determiner that the initial value of the subtraction-counter is less than zero.

The life span meter system may further comprises a detector that detects an exchange of the light source with the new light source, wherein the numerical life-span data is numerically determined from the expected life span of the light source when the exchange of the light source with the new light source is detected by the detector.

Preferably, the detector comprises a light-source-exchanging-signal generating circuit incorporated in a light-source-mounting mechanism in which the light source is detachably and exchangeably mounted, the light-source-exchanging-signal generating circuit is arranged so as to outputs a light-source-exchanging signal, indicating that the exchange of the light source with the new light source has been performed, when a mounting of the new light source in the light-source-mounting mechanism is completed and when the electronic endoscope is electrically energized.

The light-source-exchanging-signal generating circuit may be formed as a switching circuit including a voltage-applied electric line, a grounded electric line, and a movable electric contact which is arranged such that an electrical contact is established between the voltage-applied electric line and the grounded electric line when the mounting of the new light source in the light-source-mounting is completed, resulting in the outputting of the light-source-exchanging signal.

Preferably, the light-source-mounting mechanism includes a movable light-source mounting plate for mounting the light-source, a movable switching plate member, carrying the electric contact, associated with the light-source-mounting plate such that the switching plate member is moved in accordance with a movement of the light-source-mounting plate, and a locking unit for locking the switching plate member at a predetermined position during a movement of the switching plate member by the light-source mounting plate, the electrical contact being established between the voltage-applied electric line and the grounded electric line when the switching plate member is positioned and locked at the predetermined position by the locking unit.

The switching plate member may be provided with a spring unit which is arranged so as to be subjected to a compression when the switching plate member is positioned and locked at the predetermined position by the locking unit, the switching plate member being moved from the predetermined position due to the compression of the spring unit so that an electrical disconnection is established between the voltage-applied electric line and the grounded electric line when being unlocked by the locking unit.

The span meter system may further comprises another In indicator that indicates an initial adjustment of a white-balance should be performed when the exchange of the light source with the new light source is detected by the detector.

The life span meter system may further comprises yet another indicator that indicates a readjustment of a white-balance should be performed when the numerical lit-time data reaches a multiple of a pre-set numerical data over a period of said numerical life span data.

BRIEF DESCRIPTION OF THE DRAWINGS

These objects and other objects of the present invention will be better understood from the following description, with reference to the accompanying drawings in which.

DESCRIPTION OF THE PREFERRED EMBODIMENTS

Figure 1:
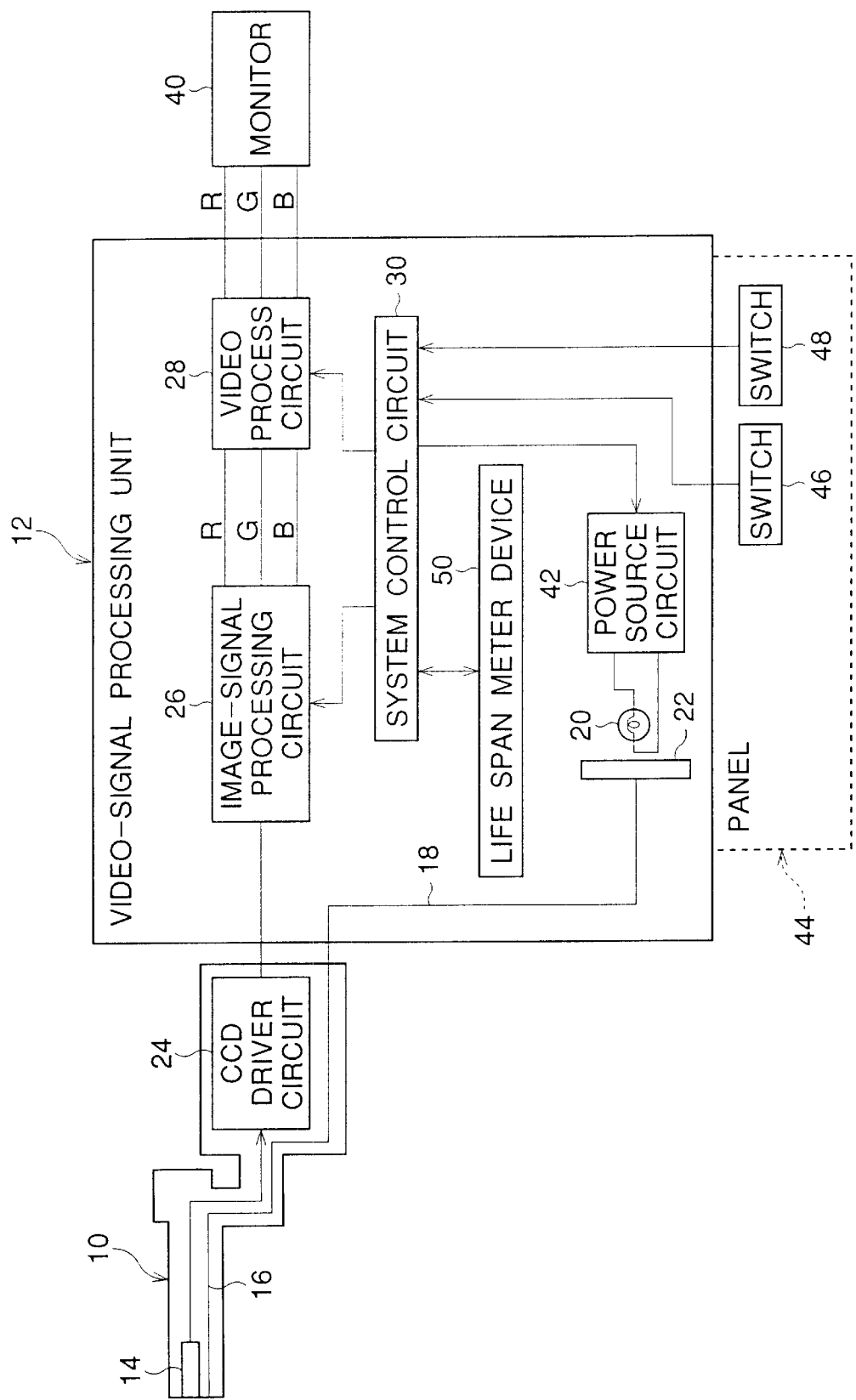
FIG. 1 is a schematic block diagram of an electronic endoscope in which a life span meter system according to the present invention is embodied.

With reference to FIG. 1, an electronic endoscope, in which a life span meter system according to the present invention is embodied, is shown as a block diagram. The electronic endoscope comprises a flexible conduit 10, and a video-signal processing unit 12 to which the flexible conduit is detachably attached.

The flexible conduit 10 includes an objective lens system (not shown) provided at the distal end thereof, and a solid image sensor 14, such as a CCD (charge-coupled device) image sensor, associated therewith. An object to be photographed is focused, as an optical image, on a light-receiving surface of the CCD image sensor 14 by the objective lens system.

The flexible conduit 10 also includes an optical light guide 16 extended therethrough and formed as a bundle of optical fibers, and the optical light guide 16 terminates at a light-emitting end face at the distal end of the flexible conduit 10. The video-signal processing unit 12 includes an optical light guide 18 formed as a bundle of optical fibers. When the flexible conduit 10 is joined to the video-signal processing unit 12, the proximal end of the optical light guide 16 of the flexible conduit 10 is optically connected to an externally-mounted end of the optical light guide 18 of the video-signal processing unit 12. The video-signal processing unit 12 also includes a light source 20, such as a xenon lamp, a halogen lamp, or the like, to which the internally-disposed end of the optical light guide 18 is optically connected. Thus, an object to be photographed by the CCD image sensor 14 is illuminated by light rays emitted from the distal end of the optical light guide 16 of the flexible conduit 10.

Note, when the flexible conduit 10 is joined to the video-signal processing unit 12, the proximal end of the optical light guide 16 of the flexible conduit 10 may be directly and optically connected to the light source 20 of the video-signal processing unit 12.

In this embodiment, for reproduction of a photographed image as a color image, an RGB field sequential-type color imaging system is incorporated in the electronic endoscope. Thus, a rotary RGB color filter 22 is intervened between the light source or lamp 20 and the inner end of the optical light guide 18 of the video-signal processing unit 12.

The rotary RGB color filter 22 is rotated at a given frequency in accordance with a used image-reproduction method, such as the NTSC method, the PAL method or the like, whereby an object to be photographed is sequentially illuminated by red light rays, green light rays and blue light rays. Namely, a red optical image, a green optical image and a blue optical image are sequentially focused on the light-receiving surface of the CCD image sensor 14 at given time intervals. Each of the red, green and blue optical images is converted into a frame of monochromatic (red, green, blue) analog image-pixel signals by the CCD image sensor 14, and the monochromatic (red, green, blue) analog image-pixel signals are successively read out of the CCD image sensor 14 by a CCD driver circuit 24 provided in the flexible conduit 10.

The video-signal processing unit 12 is provided with an image-signal processing circuit 26, which is connected to the CCD driver circuit 24 when the flexible conduit 10 is attached to the video-signal processing unit 12. The monochromatic analog image-pixel signals, read out of the CCD image sensor 14 by the CCD driver circuit 24, are fed to the image-signal processing circuit 26, in which the monochromatic image-pixel signals are subjected to various image-processings, such as a gamma-correction processing, a white-balance processing, a profile-enhancing processing and so on. Then, the processed monochromatic analog image-pixel signals are converted into monochromatic digital image-pixel signals, which are temporarily stored in a corresponding frame memory provided in the image-signal processing circuit 26.

Thereafter, the red, green and blue digital image-pixel signals are read out of the frame memories of the image-signal processing circuit 26, and are then outputted, as a series of three-primary color digital video signals (R, G and B), from the image-signal processing circuit 26 to a video process circuit 28. In short, in the image-signal processing circuit 26, the red digital video signal R, the green digital video signal G and the blue digital video signal B are produced on the basis of the red analog image-pixel signals, the green analog image-pixel signals and the blue analog image-pixel signals, respectively, read from the CCD image sensor 14 by the CCD driver circuit 24, and are then outputted to the video process circuit 28.

As shown in FIG. 1, the video-signal processing unit 12 is provided with a system control circuit 30, which may be constituted as a microcomputer, used to control the electronic endoscope as a whole, comprising, for example, a central processing unit (CPU), a read-only memory (ROM) for storing programs and constants, a random-access memory (RAM) for storing temporary data, and an input/output interface circuit (I/O). Note, of course, the reading of the monochromatic image-pixel signals from the CCD image sensor 14, the processing of the monochromatic image-pixel signals in the image-signal processing circuit 26, the production of the three-primary color digital video signals in the image-signal processing circuit 26, and the outputting of the three-primary color digital video signals from the image-processing circuit 26 to the video process circuit 28 are performed under control of the system control circuit 30.

Figure 2:
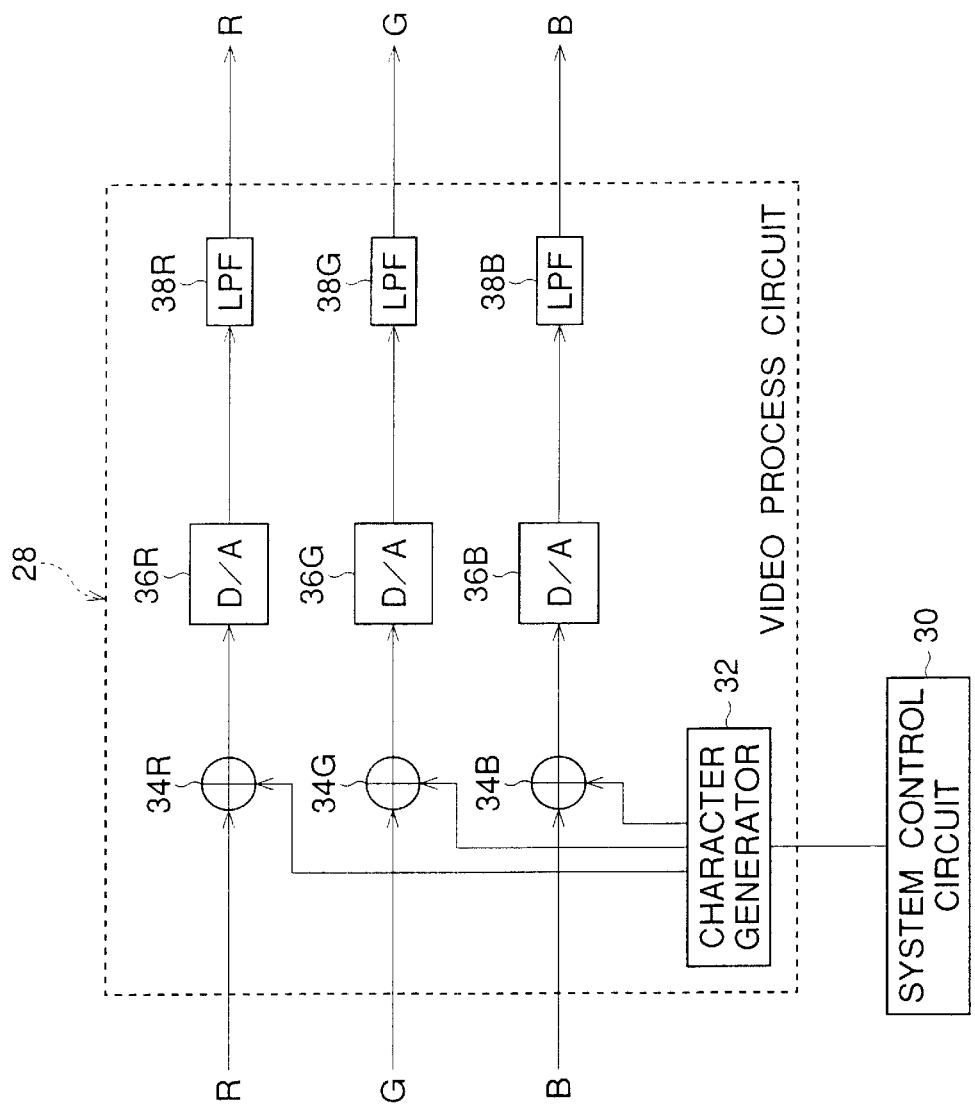
FIG. 2 is a block diagram of a video process circuit shown in FIG. 1.

FIG. 2 shows a block diagram of the video process circuit 28. As shown in this drawing, the video process circuit 28 is provided with a character generator 32 including a memory, called "a video RAM (not shown)", in which character code data are stored. The character generator 32 generates digital character pattern signals on the basis of the character code data stored in the video RAM.

As is apparent from FIG. 2, the video process circuit 28 includes digital adders 34R, 34G and 34B, which are connected to the image-signal processing circuit 26 to receive the red digital video signal R, the green digital video signal G and the blue digital video signals B therefrom, respectively, and which are connected to the character generator 32 to receive the digital character pattern signals therefrom when the character pattern signals are outputted from the character generator 32. Namely, by each of the digital adders 34R, 34G and 34B, the character pattern signals are added to the corresponding monochromatic (R, G, B) digital video signal, if necessary.

The video process circuit 28 also includes digital-to-analog (D/A) converters 36R, 36G and 36B for converting the red, green and blue digital video signals R, G and B into red, green and blue analog video signals, respectively, and low pass filters 38R, 38G and 38B for eliminating high frequency signal components from the red, green and blue analog video signals R, G and B. The red, green and blue analog video signals R, G and B are outputted from the video process circuit 28, and therefore from the video-signal processing unit 12, to a monitor 40 (FIG. 1) to reproduce and display the photographed color image thereon. Of course, when the red, green and blue analog video signals R, G and B carry the character pattern signals, character information data based on the character pattern signals are displayed together with the reproduced color image on the monitor 40.

The character information data to be displayed on the monitor is classified into two groups: one group of variable character information data, such as a patient's name, a date and time of examination, examination comments and so on; and the other group of fixed character information data concerns warning messages, such as "EXCHANGE OF LAMP", and "ADJUSTMENT OF WHITE BALANCE", which especially relate to the present invention. The variable character code data corresponding to the variable character information data are written in the video RAM of the character generator 32 through a keyboard (not shown), connected to the video process circuit 28 via the system control circuit 30, if necessary. On the other hand, the fixed character code data corresponding to the fixed character information data are previously stored in the ROM of the system control circuit 30. If necessary, the fixed character code data are read from the ROM of the system control circuit 30, and are then written in the video RAM of the character generator 32.

As shown in FIG. 1, the video-signal processing unit 12 is provided with an electric power source circuit 42, by which the lamp 20 is electrically energized under control of the system control circuit 30. Also, the video-signal processing unit 12 is provided with a manipulation panel 44, conceptually shown by a dotted line in FIG. 1, in which various switches are provided. In this drawing, a power ON/OFF switch 46 for the video-signal processing unit 12 and a lamp ON/OFF switch 48 for the lamp 20, which especially relate to the present invention, are illustrated.

Figure 3:
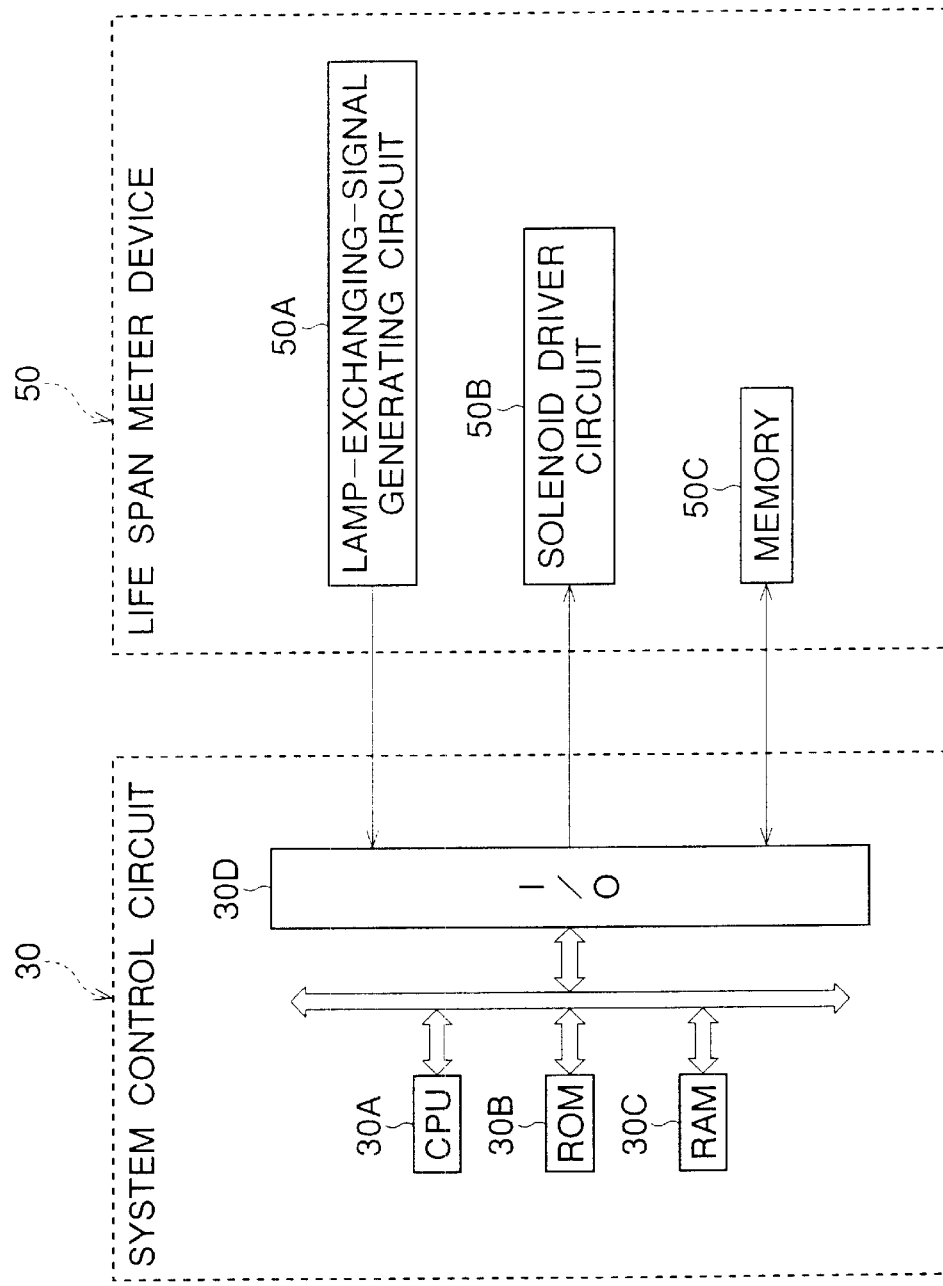
FIG. 3 is a block diagram of a system control circuit and a life span meter device shown in FIG. 1.

Further, the video-signal processing unit 12 is provided with a life span meter device 50 for calculating a remaining life span of the lamp source 20, which is operated under control of the system control circuit 30. As shown in FIG. 3, the life span meter device 50 includes a lamp-exchanging-signal generating circuit 50A, a solenoid driver circuit 50B, and a non-volatile memory 50C, and these elements 50A, 50B and 50C will be discussed in detail hereinafter.

Note, in FIG. 3, the CPU, ROM, RAM and I/O of the system control circuit 30 are indicated by references 30A, 30B, 30C and 30D, respectively.

Figure 4:
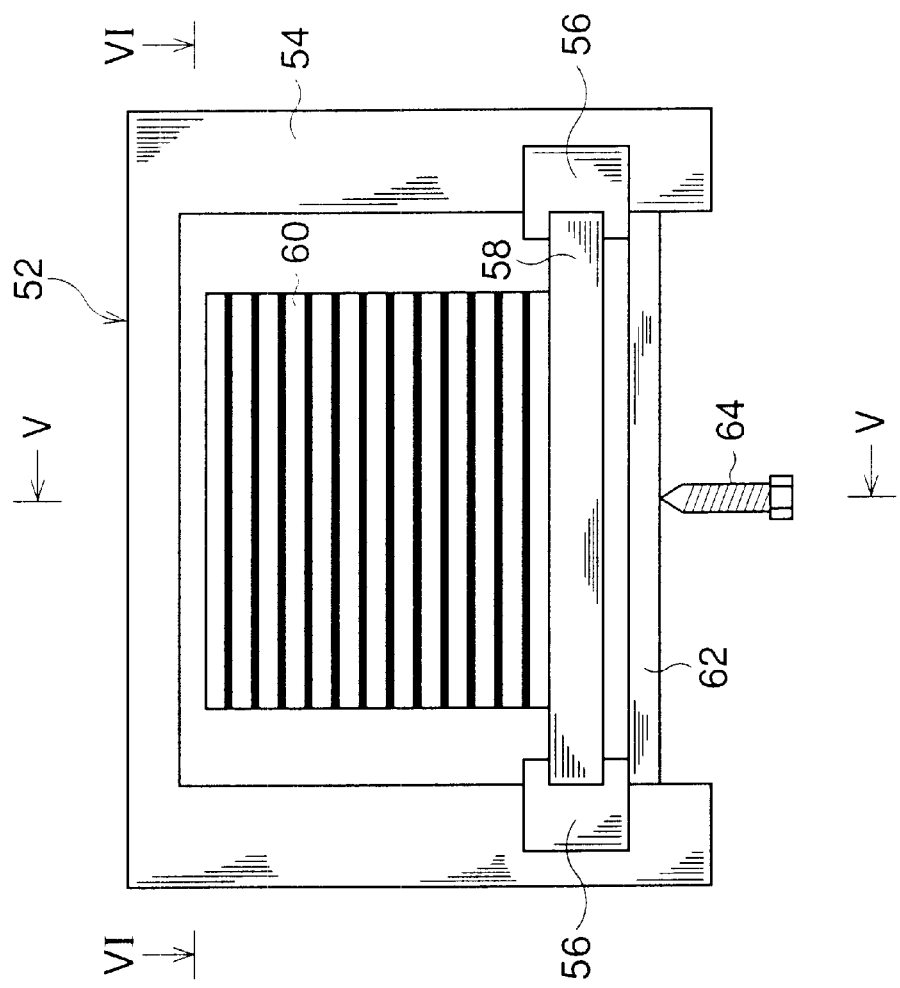
FIG. 4 is a schematic front view partially showing a lamp-mounting mechanism for detachably and exchangeably mounting a light source lamp shown in FIG. 1.
Figure 5:
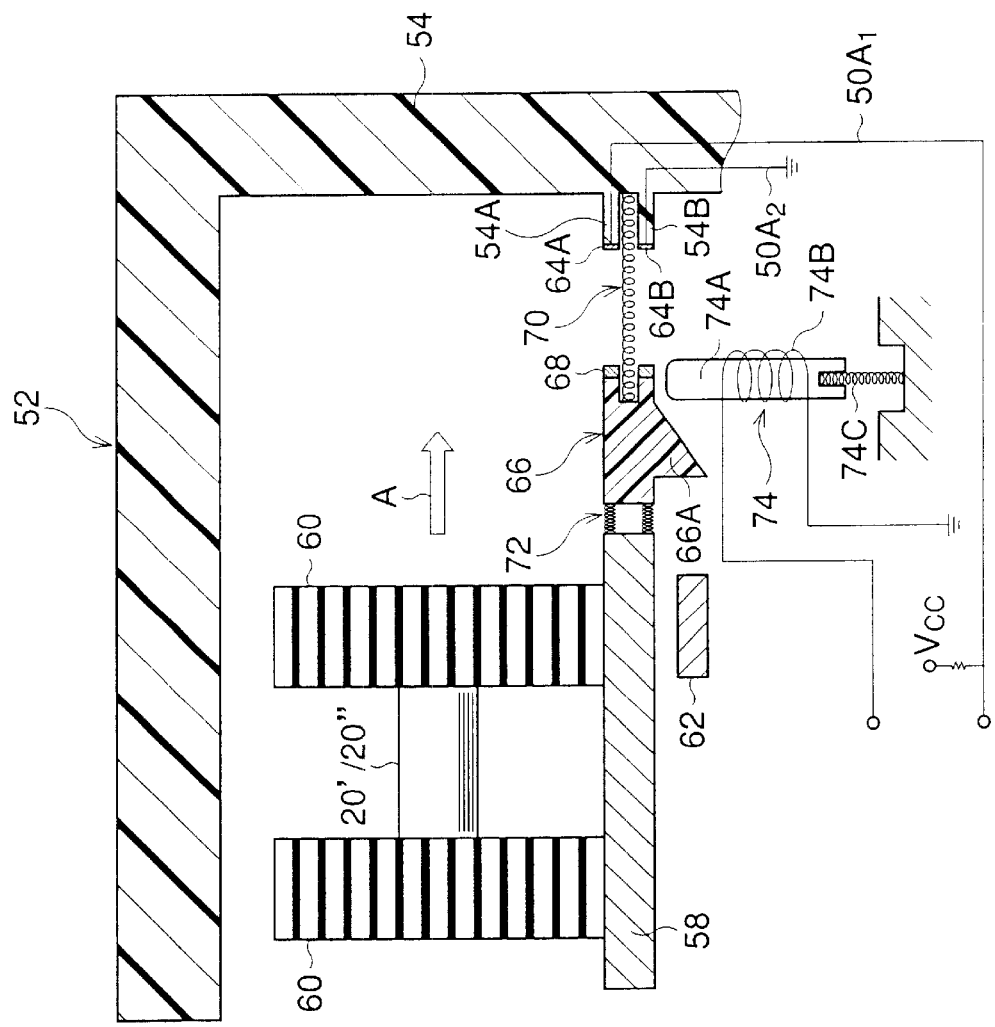
FIG. 5 is a longitudinally-sectioned view taken along a line V—V of FIG. 4.
Figure 6:
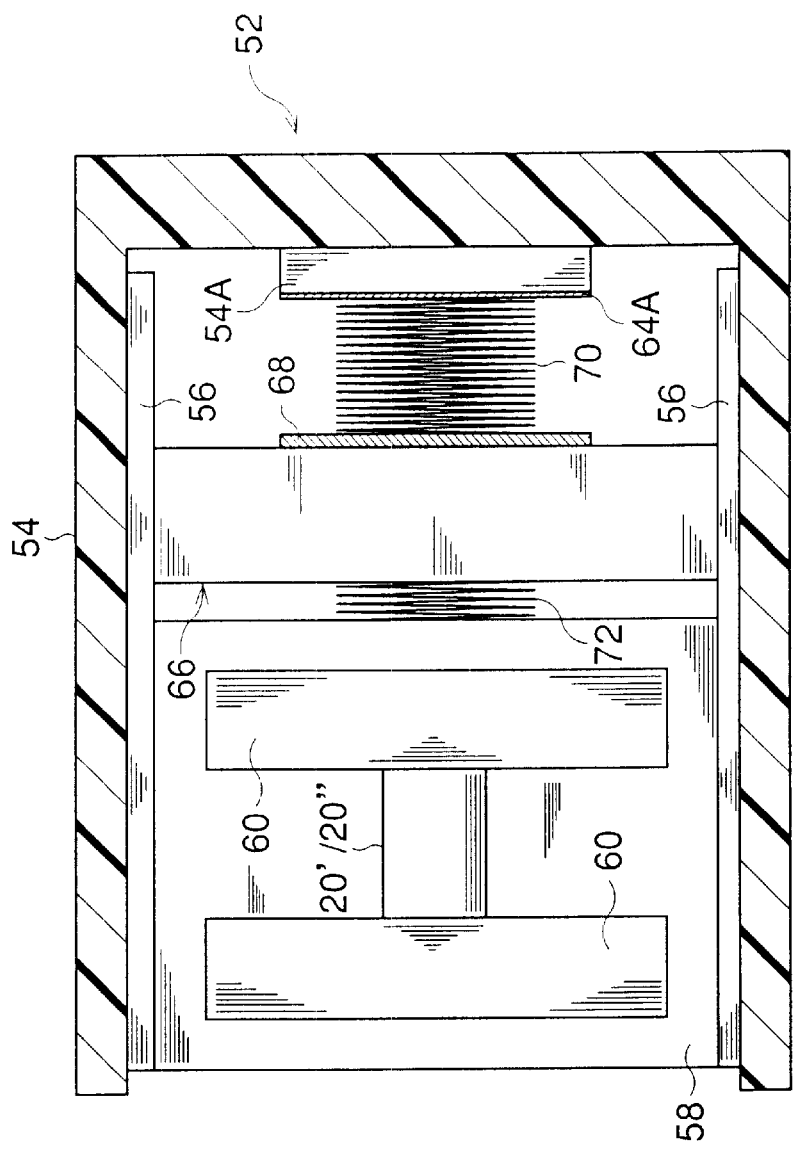
FIG. 6 is a horizontally-sectioned plan view taken along a line VI—VI of FIG. 4.

FIGS. 4 to 6 show a lamp-mounting mechanism 52 for detachably and exchangeably mounting the lamp 20, which forms a part of a physical structure of the video-signal processing unit 12. The lamp-mounting mechanism 52 includes a box-shaped lamp housing 54 provided in the video-signal processing unit 12. The lamp housing 54 is integrally formed from a suitable electrically-insulating material, such as a synthetic resin material that exhibits a high heat-resistance, and has a top wall, opposing side walls, a closed end-face and an open end-face.

The open end-face of the lamp housing 54, as shown in FIGS. 4 and 6, is accessible by removing a part of a housing wall of the video-signal processing unit 12. The lamp housing 54 is provided with a pair of guide rails 56, which are partially and securely embedded in inner surfaces of opposing side walls of the lamp housing 54, respectively, so as to horizontally coextend along a longitudinal length of the opposing side walls of the lamp housing 54. As best shown in FIG. 4, each of the guide rails 56 has a guide groove extending along a length thereof, and a lamp mounting plate 58 is provided in the lamp housing 54 such that opposing side edges of the lamp mounting plate 58 are slidably received in the opposing guide grooves of the guide rails 56, whereby the lamp mounting plate 58 is movable along the pair of guide rails 56.

A pair of heat sinks 60 is detachably mounted on the lamp mounting plate 58 by suitable fasteners, such as screws (not shown), and the lamp 20 is supported by the heat sinks 60 so as to extend therebetween. When the lamp 20 is exchanged with a new lamp 20', the lamp mounting plate 58 carrying the heat sinks 60 and the lamp 20 is removed from the housing of the video-signal processing unit 12, whereby the exchange of the lamp 20 with the new lamp 20' can be easily carried out by detaching the heat sinks 60 from the lamp mounting plate 58.

After the exchange of the lamp 20 with the new lamp 20' is completed, the lamp mounting plate 58 carrying the heat sinks 60 and the new lamp 20' is introduced into the lamp housing 54 along the guide rails 56, and is then positioned and fixed at a predetermined position. To this end, a positioning-strip plate 62 bridges the opposing side walls of the lamp housing 54 at a given location along and below the guide rails 56, as shown in FIGS. 4 and 5, and the lamp mounting plate 58 is fixed to the positioning-strip plate 62 by a screw 64 (FIG. 4).

In particular, the lamp mounting plate 62 has a threaded hole formed therethrough, and the positioning-strip plate 62 has a smooth hole formed therethrough. When the lamp mounting plate 58 is moved along the guide rails 56, and is positioned at the predetermined position, the threaded hole of the lamp mounting plate 58 is aligned with the smooth hole of the positioning-strip plate 62, and then the screw 64 is screwed into the threaded hole of the plate 58 through the smooth hole of the plate 62.

The lamp-exchanging-signal generating circuit 50A of the life span meter device 50 (FIG. 3) is incorporated, as a switching circuit, in the lamp-mounting mechanism 52, and is arranged so as to output a lamp-exchanging signal, indicating that the exchange of the lamp 20 with the new lamp 20' has been performed, from the circuit 50A to I/O 30D whenever the lamp mounting plate 58 carrying the heat sinks 60 and the exchanged lamp 20' is introduced into the lamp housing 54 along the guide rails 56, and is fixed at the predetermined position in accordance with a proper procedure as stated in detail hereinafter.

The closed end-face of the lamp housing 54 is formed with a pair of elongated-plate projections 54A and 54B integrally protruding from the inner wall surface thereof, and the elongated-plate projections 54A and 54B are spaced part from each other. The elongated-plate projections 54A and 54B are provided with electrode elements 64A and 64B, respectively, attached to the free end-faces thereof, and the electrode elements 64A and 64B form a part of the lamp-exchanging-signal generating circuit(hereinafter: switching circuit) 50A.

The switching circuit 50A includes an electric line $50A_1$ to which a given voltage ($V_{cc}$) is applied through a suitable electric resistance symbolically shown in FIG. 5. One end of the electric line $50A_1$ is connected to the electrode element 64A, and the other end thereof is connected to I/O 30D (FIG. 3) to feed the lamp-exchanging signal to the system control circuit 30. The switching circuit 50A also includes an electric line $50A_2$ connected at one end thereof to the electrode elements 64B, and which is grounded at the other end thereof.

Note, in a state as shown in FIG. 5, the lamp-exchanging signal is inputted as a high level signal to I/O 30D through the electric line $50A_1$, due to the application of the voltage ($V_{cc}$) to the electric line $50A_1$, and due to an electrical disconnection between the electrode elements 64A and 64B.

The switching circuit 50A further includes a movable switching plate member 66 formed from an electrically-insulating material, such as a suitable synthetic resin. As best shown in FIG. 6, the movable switching plate member 66 has an elongated plate-shape, and is arranged between the positioning-strip plate 62 and the elongated-plate projections 54A and 54B. Similar to the lamp mounting plate 58, the opposing lateral side edges of the switching plate member 66 are slidably received in the grooves of the guide rails 56 so that the switching plate member 66 is movable along the length of the guide rails 56. The switching plate member 66 is provided with an electric elongated annular contact 68 securely attached to one of the longitudinal side edges thereof, facing the closed end-face of the lamp housing 54. The electric annular contact 68 has a size that matches the pair of elongated plate-like projections 54A and 54B, and is aligned therewith.

As shown in FIGS. 5 and 6, the switching plate member 66 is provided with a first spring 70 and a second spring 72, by which a movement of the switching plate member 66 along the guide rails 56 is regulated in a manner as stated in detail hereinafter. Note, in FIGS. 5 and 6, the first and second springs 70 and 72 are symbolically illustrated.

The first spring 70 is disposed and constrained between the switching plate member 66 and the pair of elongated-plate projections 54A and 54B. The second spring 72 is securely attached to an opposing longitudinal side edge of the movable switching plate member 66, opposite the side edge thereof to which the electric elongated annular contact 68 is attached, and thus the lamp mounting plate 58 abuts the second spring 72 when being introduced into the lamp housing 54 along the guide rails 56, as shown in FIGS. 5 and 6.

As shown in FIG. 5, the lamp mounting mechanism 52 is provided with an electromagnetic solenoid actuator 74 which is electrically energized by the solenoid driver circuit 50B of the life span meter device 50 (FIG. 3), and the solenoid actuator 74 is operated in conjunction with a wedged stopper 66A integrally projecting from the movable switching plate member 66 in a manner as stated hereinafter.

The solenoid actuator 74 includes a plunger 74A, an electromagnetic solenoid 74B surrounding the plunger 74A, and a compressed coil spring 74C associated with the plunger 74A. The electromagnetic solenoid 74B is electrically connected to the solenoid driver circuit 50B, and is electrically energized thereby under control of the system control circuit 30. When the solenoid 74B is not electrically energized, the plunger 74A is resiliently biased in a protruded position, as shown in FIG. 5, due to a resilient force resulting from the compressed coil spring 74C. When the electrical energization of the solenoid 74B is performed, the plunger 74A is retracted from the protruded position (FIG. 5) against the resilient force of the compressed coil spring 74C. As is apparent from FIG. 5, when the plunger 74A is at the protruded position, the plunger 74A can be engaged with the wedged stopper 66A of the movable switching plate member 66.

The above-mentioned lamp mounting mechanism 52 is operated as follows:

During the introduction of the lamp mounting plate 58, carrying the heat sinks 60 and the exchanged lamp 20', into the lamp housing 54 along the guide rails 56, the lamp mounting plate 58 abuts the second spring 72, as shown in FIG. 5. When the lamp mounting plate 58 is further advanced in a direction indicated by an arrow A in FIG. 5, the second spring 72 is compressed so that the switching plate member 66 is moved toward the pair of elongated-plate projections 54A and 54B, resulting in a compression of the first spring 70.

During the movement of the switching plate member 66 toward the pair of elongated-plate projections 54A and 54B, although a slant face of the wedged stopper 66A abuts a rounded top end of the plunger 74A, the wedged stopper 66A can clear the rounded top end of the plunger 74A, due to the slant face thereof. Namely, the plunger 74A is depressed from the protruded position (FIG. 5), due to it being subjected to a depression force by the abutment of the slant face of the wedged stopper 66A against the rounded top end of the plunger 74A, whereby the wedged stopper 66A can clear the rounded top end of the plunger 74A.

Figure 7:
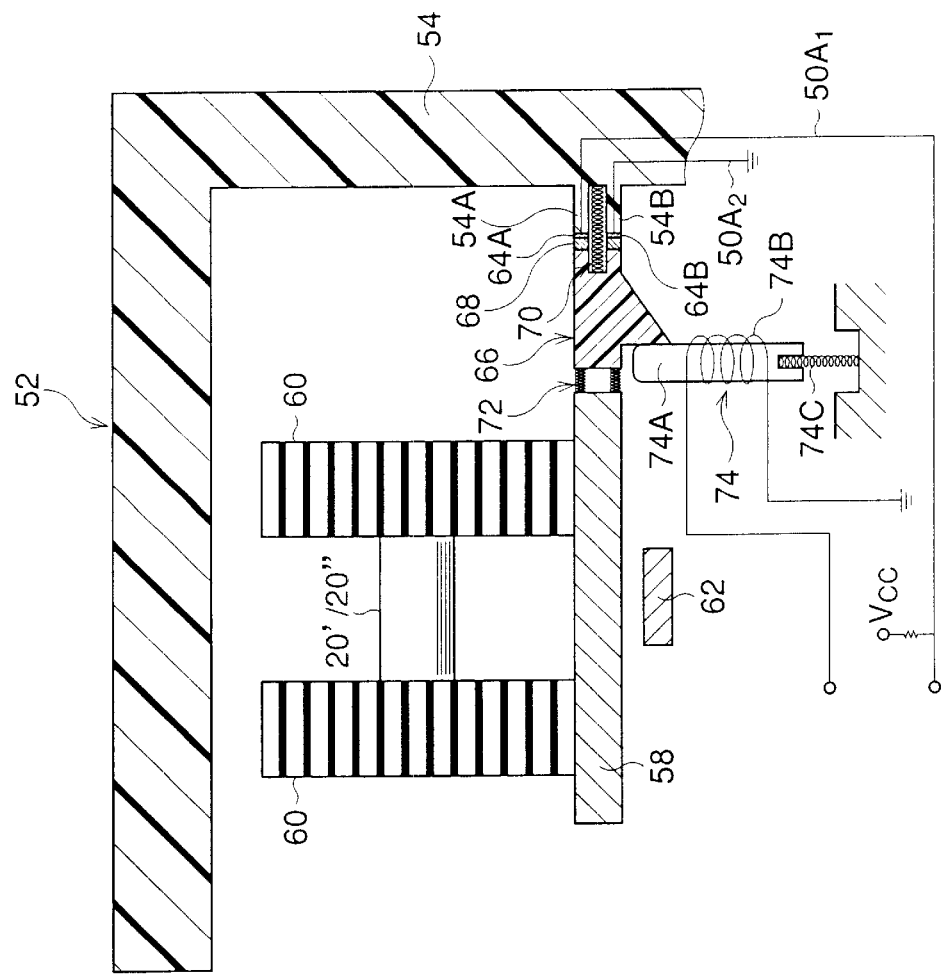
FIG. 7 is a longitudinally-sectioned view, similar to FIG. 5, showing a step in a mounting-procedure of the light source lamp.

As shown in FIG. 7, as soon as the wedged stopper 66A clears the rounded top end of the plunger 74A, the depressed plunger 74A returns to the protruded position due to the resilient force resulting from the compressed coil spring 74C, and the plunger 74A is engaged with a vertical face of the wedged stopper 66A, whereby the movable switching plate member 66 is locked at a position as shown in FIG. 7.

When the movable switching plate member 66 is locked at the position shown in FIG. 7, the elongated annular contact 68 is in contact with the electrode elements 64A and 64B of the elongated-plate projections 54A and 54B, whereby the electrode elements 64A and 64B are electrically connected to each other. Thus, the lamp-exchanging signal, inputted to I/O 30D of the system control circuit 30 through the electric line 50A$_1$, is changed from the high level to a low level, due to the electrical connection between the electrode elements 64A and 64B. Note, the change of the lamp-exchanging-signal from the high level to the low level indicates that the exchange of the lamp 20 with the new lamp 20' has been performed.

Figure 8:
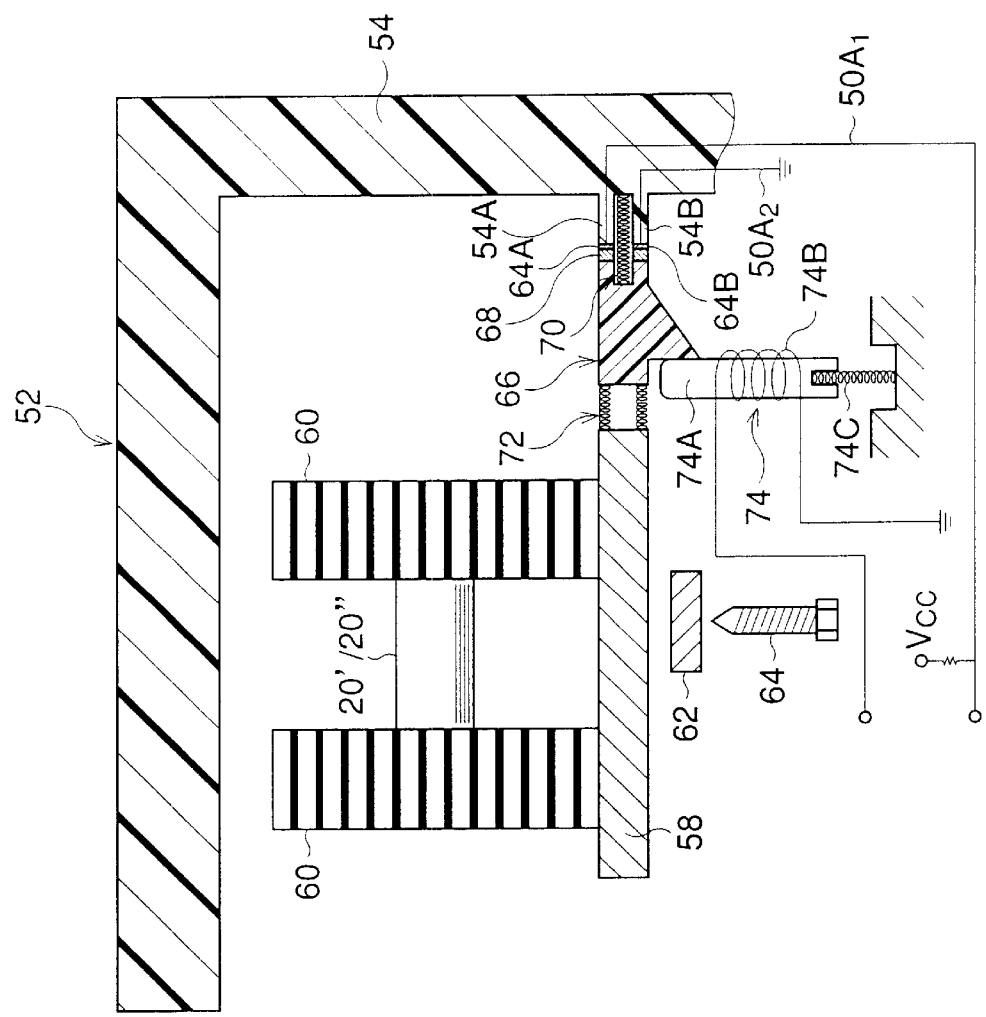
FIG. 8 is a longitudinally-sectioned view, similar to FIG. 5, showing another step in the mounting-procedure of the light source lamp.

Also, after the movable switching plate member 66 is locked at the position shown in FIG. 7, the lamp mounting plate 58 is retracted until the threaded hole of the lamp mounting plate 58 aligns with the smooth hole of the positioning-strip plate 62, as shown in FIG. 8, and the screw 64 is then engaged with the threaded hole through the smooth hole of the positioning-strip plate 62, whereby the fixing of the lamp mounting plate 58 to the positioning-strip plate 62 at the predetermined position is completed.

After the fixing of the lamp mounting plate 58 is completed, the part of the housing wall of the video-signal processing unit 12, which is removed to access the open end-face of the lamp housing 54 (FIG. 4), is reattached to the housing wall to close the open end-face. Thus, the video-signal processing unit 12 is now able to e utilized.

Figure 9:
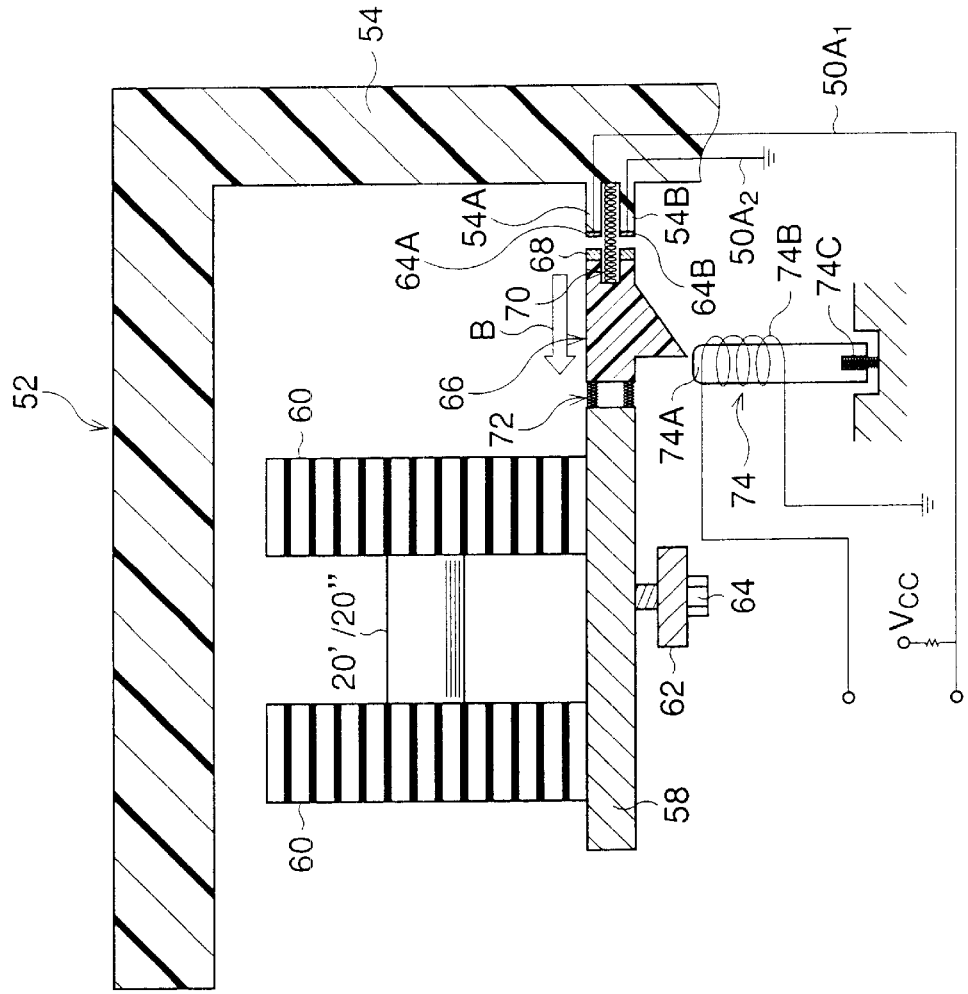
FIG. 9 is a longitudinally-sectioned view, similar to FIG. 5, showing yet another step in the mounting-procedure of the light source lamp.

Thereafter, when the power ON/OFF switch 46 (FIG. 1) and the lamp ON/OFF switch 48 are turned ON, the solenoid actuator 74 is electrically energized, as stated in detail hereinafter, so that the plunger 74A is retracted from the protruded position (FIG. 8) to a position as shown in FIG. 9, whereby the wedged stopper 66A of the switching plate 66 is disengaged from the plunger 74A. Since the resilient force of the first spring 70 is larger than that of the second spring 72 in the state shown in FIG. 8, the switching plate 66 moves back in a direction indicated by an arrow B in FIG. 9 due to the disengagement of the wedged stopper 66A from the plunger 74A, whereby the electric annular contact 68 is separated from the pair of electrode elements 64A and 64B, so that these electrode elements 64A and 64B are electrically disconnected from each other, resulting in a change of the lamp-exchanging-signal from the low level to the high level.

With the arrangement of the above-mentioned lamp-exchanging-signal generating circuit or switching circuit 50A, it is possible to surely detect, via the system control circuit 30, whether the lamp 20 has been exchanged with the new lamp 20' whenever the power ON/OFF switch 46 is turned ON.

As mentioned above, the life span meter device 50 includes the non-volatile memory 50C, which may be an electrically-erasable and programmable read-only memory (EEPROM). As stated hereinafter, the non-volatile memory 50C stores various data, which cannot be, of course, lost by turning the power ON/OFF switch 46 OFF.

Figure 10:
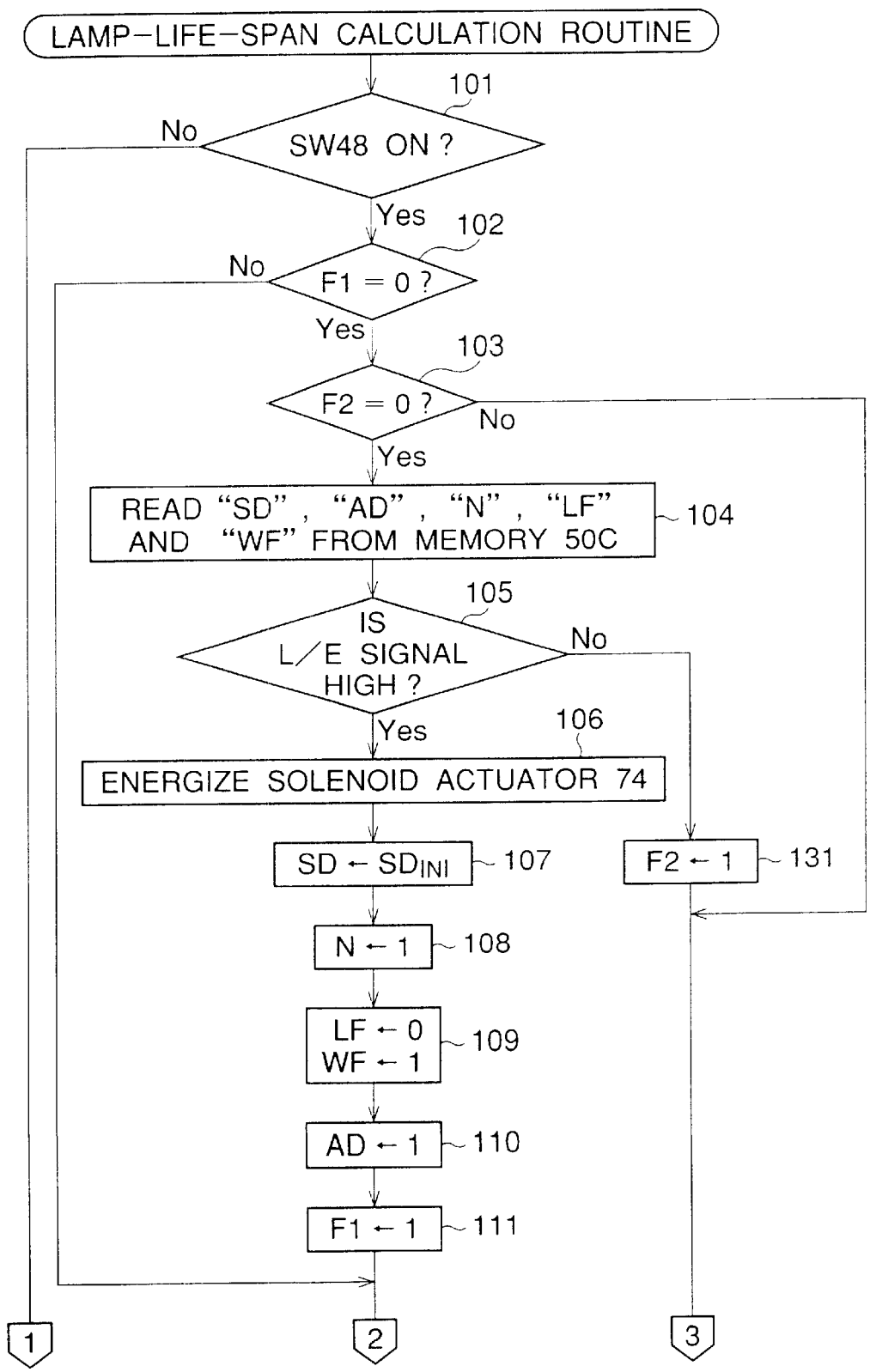
FIG. 10 is a part of a flowchart showing a remaining-lamp-life-span calculation routine executed in the life span meter system according to the present invention.
Figure 11:
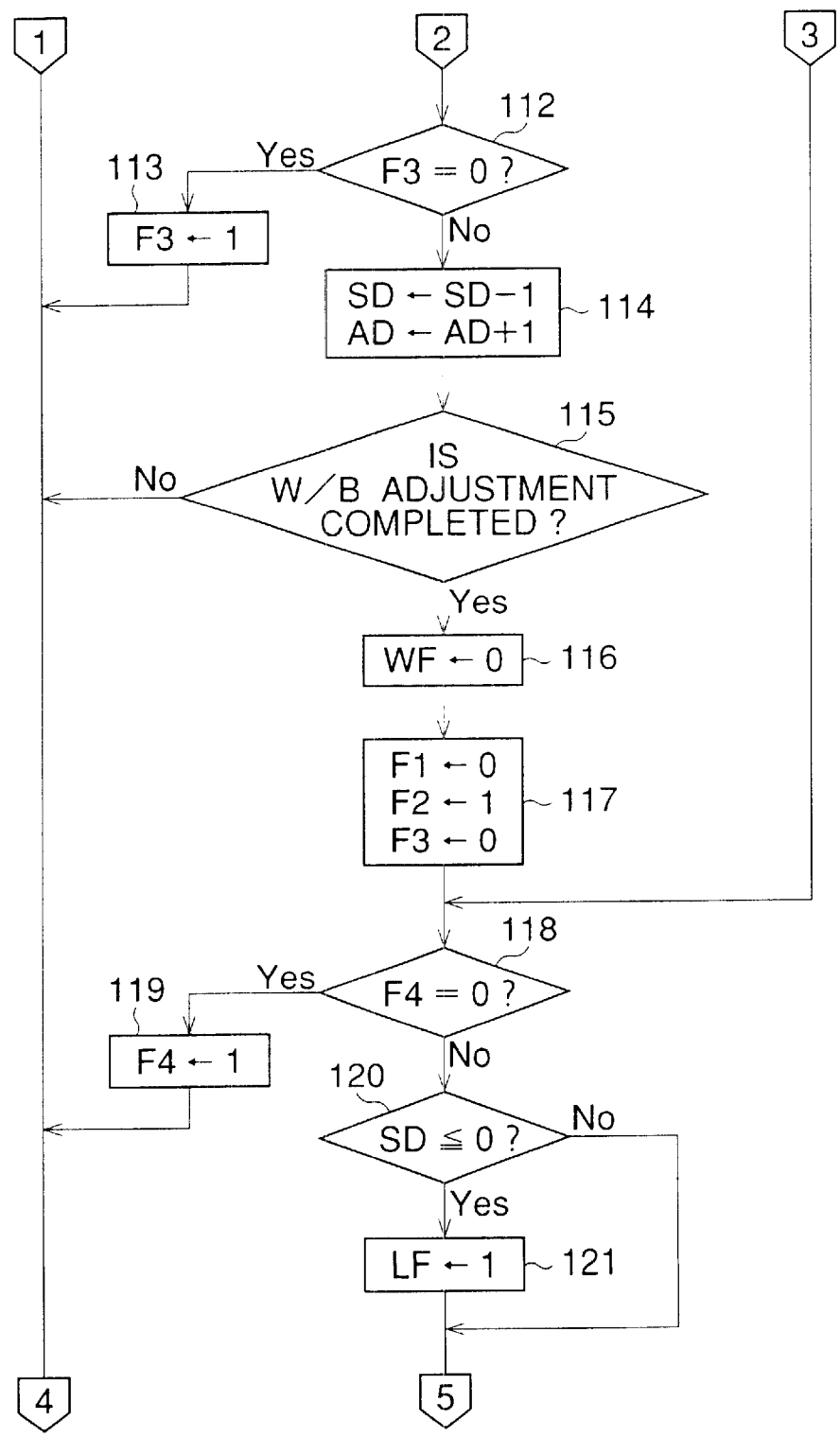
FIG. 11 is another part of the flowchart showing the remaining-lamp-life-span calculation routine executed in the life span meter system according to the present invention.
Figure 12:
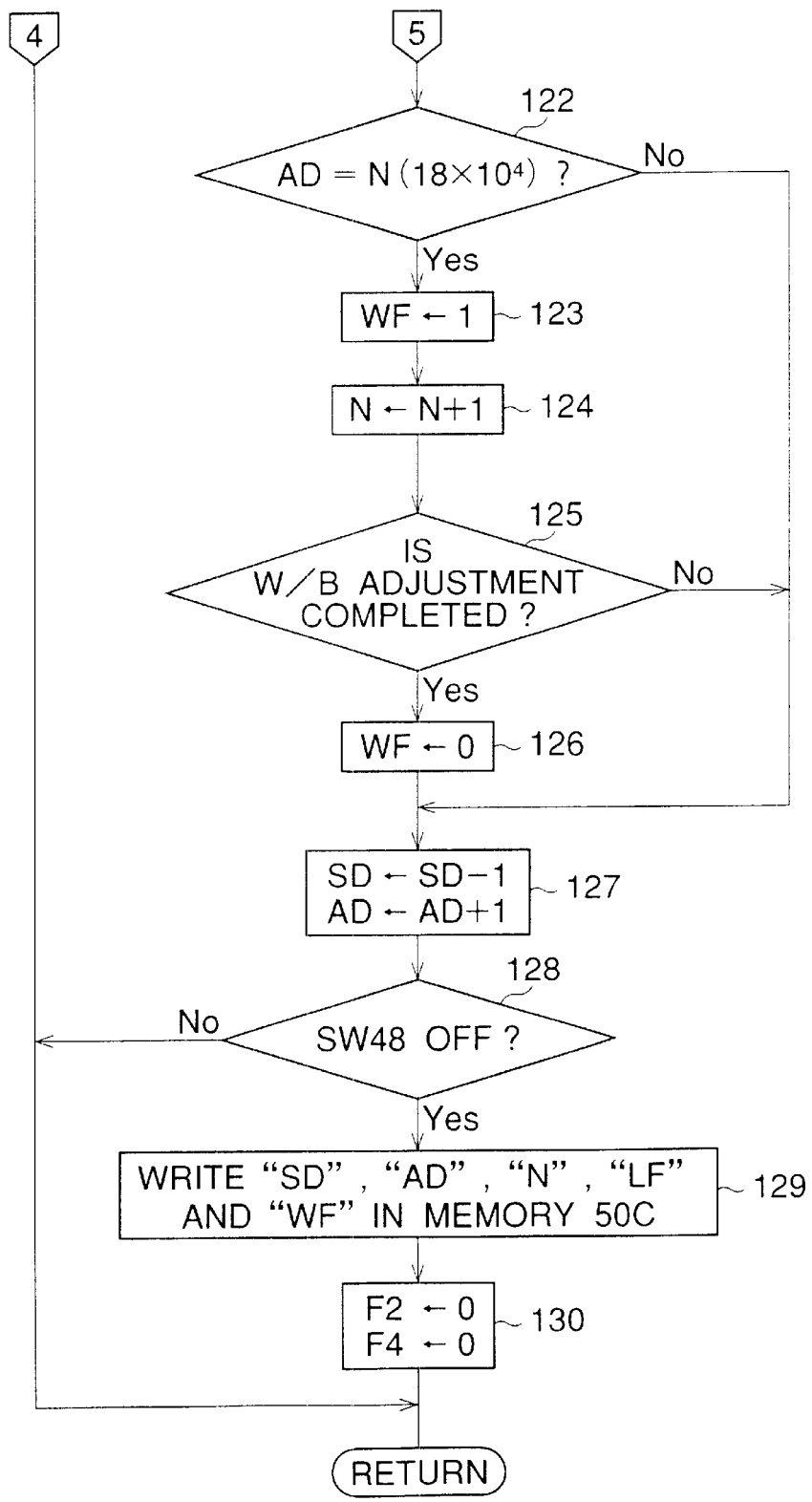
FIG. 12 is the remaining part of the flowchart showing the remaining-lamp-life-span calculation routine executed in the life span meter system according to the present invention.

FIGS. 10, 11 and 12 shows a flowchart of a lamp-life-span calculation routine executed by the system control circuit 30. This lamp-life-span calculation routine is constituted as a time-interruption routine which is repeatedly executed at regular intervals of, for example, one second, and the execution of this routine is started by turning the power ON/OFF switch 46 ON.

At step 101, it is determined whether the lamp ON/OFF switch 48 is turned ON. If the switch 48 is OFF, the routine once ends. Although the routine is repeatedly executed at the regular intervals of one second, there is no progress as long as the switch 48 is OFF. Namely, at step 101, it is monitored whether the lamp ON/OFF switch 48 is turned ON.

When it is confirmed that the switch 48 is turned ON at step 101, the control proceeds to step 102, in which it is determined whether a flag F1 is "0" or "1". At an initial stage, when the power ON/OFF switch 46 has been turned ON, since a flag F1 is set to "0", the control proceeds to step 103, in which it is determined whether a flag F2 is "0" or "1". Similar to the flag F1, at the initial stage, since F2=0, the control proceeds to step 104. Note, each of the flags F1 and F2 is defined at a given address in RAM 30C of the system control 30.

At step 104, a subtraction-data SD, an addition-data AD, a variable data N, an lamp-exchanging-demand flag LF, and a white-balance-adjustment-demand flag WF are read from the non-volatile memory 50C, and are stored in the RAM 30C of the system control circuit 30. Note, the subtraction-data SD represents a remaining life span of the lamp 20, the addition-data AD represents a total lit-time of the lamp 20, and the variable data N represents a point at which the white-balance should be adjusted. Also, note, the lamp-exchanging-demand flag LF is to determine whether the previously mentioned warning message "EXCHANGE OF LAMP" should be displayed on the monitor 40, and the white-balance-adjustment-demand flag WF is to determine whether the previously mentioned warning message "ADJUSTMENT OF WHITE BALANCE" should be displayed on the monitor 40.

At step 105, it is determined whether the lamp-exchanging signal, inputted to I/O 30D of the system control circuit 30 through the electric line 50A$_1$, is low. Note, as mentioned previously, if the lamp-exchanging signal is low, this indicates that the lamp 20 has been exchanged with a new lamp 20'. When the lamp-exchanging signal is low, the control proceeds to step 106, in which the electromagnetic solenoid actuator 74 is electrically energized by the solenoid driver circuit 50B for a predetermined period. Thus, as mentioned above, the wedged stopper 66A of the movable switching plate 66 is disengaged from the plunger 74A of the solenoid actuator 74, whereby the switching plate 66 retreats in the direction indicated by the arrow B in FIG. 9, resulting in the electrical disconnection of the electrode elements 58A and 58B, so that the lamp-exchanging signal is changed from the low level to the high level.

At step 107, the subtraction-counter SD is initialized by an initial data $SD_{INI}$, which is numerically evaluated from a an expected useful life span of the exchanged new lamp 20'. For example, in general, when the exchanged new lamp 20' is a xenon lamp, the expected useful life span is of an order of about 300 hours, and, when the exchanged new lamp 20' is a halogen lamp, the expected useful life span is of an order of about 60 hours. In this embodiment, since it is intended that the xenon lamp is utilized for the lamp (20, 20'), the initial data $SD_{INI}$ corresponds to a numerical value of $108 \times 10^4$[300 (hr.)$\times$60 (sec.)$\times$60 (min.)]. Note, the initial data $SD_{INI}$ is previously stored as a fixed data in the ROM 30B of the system control circuit 30.

At step 108, the variable data N is initialized to "1". Then, at step 109, the lamp-exchanging-demand flag LF is made to be "0", and the white-balance-adjustment-demand flag WF is made to be "1". Accordingly, the fixed character code data, corresponding to the warning message "ADJUSTMENT OF WHITE BALANCE", is read from the ROM 30B of the system control circuit 30, and is then written in the video RAM of the character generator 32, whereby the character generator 32 generates digital red, green and blue character pattern signals on the basis of the fixed character code data written in the video RAM, and then feeds these digital pattern signals to the digital adders 34R, 34G and 34B. Thus, the warning message "ADJUSTMENT OF WHITE BALANCE" is displayed on the monitor 40. Namely, by displaying the warning message "ADJUSTMENT OF WHITE BALANCE" on the monitor 40, it is announced that an initial adjustment of the white balance is necessary due to the exchange of the lamp 20 with the new lamp 20'.

At step 110, the addition-data AD is initialized to "1", and, at step 111, the flag F1 is made from "0" to "1". Then, at step 112, it is determined whether a flag F3 is "0" or "1". Similar to the flags F1 and F2, at the initial stage, since F3=0, the control proceeds to step 113, in which the flag F3 is made to be "1". Note, the flag F3 is also defined at a given address in the RAM 30C of the system control 30.

After the flag F3 is made to be "1" at step 113, the outline once ends. When the routine is again executed after the second has elapsed, the control jumps from step 102 to step 112 (F1=1), in which it is determined whether the flag F3 is "0" or "1". At this stage, since F3=1 (step 113), the control proceeds from step 112 to step 114, in which the following calculations are executed:

SD←SD−1

AD←AD+1

Namely, the subtraction-data SD is decremented by "1", and the addition-data AD is incremented by "1". In short, the counting of the total lit-time of the new lamp 20' is commenced at a unit of one second, and the counting of the point, at which the white-balance should be adjusted, is also commenced at a unit of one second.

Note, steps 112 and 113 (the flag F3) are provided to avoid the decrementing of the subtraction-data SD and the incrementing of the addition-data AD during a first execution of the routine subsequent to the turning-ON of the lamp ON/OFF switch 48, whereby the counting of the subtraction-data SD and the addition-data AD can be correctly performed.

Then, at step 115, it is determined whether the initial adjustment of the white-balance is completed. When the initial adjustment of the white-balance has not been completed, the routine once ends. Although the execution of the routine is repeated at the regular intervals of one second, the above-mentioned calculations (step 114) are merely executed every one second until the initial adjustment of the white-balance is completed.

Note, in electronic endoscopes, an adjustment of the white-balance per se is well known. In short, an operation mode is switched from a usual operation mode to a white-balance-adjustment operation mode in a video-signal processing unit (12), and a distal end of a flexible conduit (10) is inserted into a tubular-like envelope, an inner wall surface of which is coated with a standard white pigment layer. Then, a series of red image-pixel signals, a series of green image-pixel signals and a series of blue image-pixel signals are obtained from a CCD image sensor (14), and a red image correction data, a green image correction data and a blue image correction data, which are used for the white-balance processing, are prepared on the basis of the red, green and blue image-pixel signals derived from the standard white pigment layer of the tubular-like envelope. After the adjustment of the white-balance is completed, the operation mode is returned from the white-balance-adjustment operation mode to the usual operation mode in the video-signal processing unit (12).

At step 115, when it is confirmed that the adjustment of the white-balance has been completed, the control proceeds to step 116, in which the white-balance-adjustment-demand flag WF is made to be "0", whereby the warning message "ADJUSTMENT OF WHITE BALANCE" is deleted from the monitor 40. Then, at step 117, the flag F1 is made to be "0"; the flag F2 is made to be "1"; and the flag F3 is made to be FIX.

At step 118, it is determined whether a flag F4 is "0" or "1". Similar to the flags F1, F2 and F3, at the initial stage, since F4=0, the control proceeds to step 119, in which the flag F4 is made to be "1". Note, the flag F4 is also defined at a given address in the RAM 30C of the system control 30.

After the flag F4 is made to be "1" at step 119, the routine once ends. When the routine is again executed after one second has elapsed, the control jumps from step 103 to step 118 (F2=1), in which it is determined whether the flag F4 is "0" or "1". At this stage, since F4=1 (step 119), the control proceeds from step 118 to step 120, in which it is determined whether the subtraction-data SD has been decremented to zero. If SD>0, i.e. if a total lit-time of the lamp 20' has not reached the useful life span of the exchanged lamp 20' corresponding to the numerical value ($SD_{INI}=108\times10^4$), the control skips step 121 to step 122.

On the other hand, at step 120, if SD≦0, i.e. if a total lit-time of the lamp 20' has reached or exceeded the useful life span of the exchanged lamp 20' corresponding to the numerical value ($SD_{INI}=108\times10^4$), the control proceeds from step 120 to step 121, in which the lamp-exchanging-demand flag LF is made to be "1". Accordingly, the fixed character code data, corresponding to the warning message "EXCHANGE OF LAMP", is read from the ROM 30B of the system control circuit 30, and is then written in the video RAM of the character generator 32, whereby the character generator 32 generates red, green and blue digital character pattern signals on the basis of the fixed character code data written in the video RAM, and then feeds the digital pattern signals to the digital adders 34R, 34G and 34B. Thus, the warning message "EXCHANGE OF LAMP" is displayed on the monitor 40. Namely, by displaying the warning message "EXCHANGE OF LAMP" on the monitor 40, it is announced that an exchange of the lamp 20' with a new lamp 20" is necessary. After the lamp-exchanging-demand flag LF is made to be "1", the control proceeds to step 122.

Note, of course, the exchange of the lamp 20' with the new lamp 20" is carried out in the same manner as explained with reference to FIGS. 5 to 9.

At step 122, it is determined whether the addition-data AD has been incremented to a numerical value $N(18 \times 10_4)$ corresponding to a multiple of 50 [50 (hr.)×60 (sec.)×60 (min.)] hours. In this embodiment, it is intended that the adjustment of the white-balance should be performed every 50 hours. If $AD \neq N(18 \times 10^4)$, e.g. if the total-lit time of the lamp 20' has not reached 50 hours (N=1) from the exchange of the lamp 20 with the new lamp 20', the control skips from 122 to step 127.

On the other hand, at step 122, if $AD = N(18 \times 10_4)$, e.g. if the total-lit time of the lamp 20' has reached 50 hours from the exchange of the lamp 20 with the new lamp 20', the control proceeds to step 123, in which the white-balance-adjustment-demand flag WF is made to be "1". Accordingly, as already mentioned above, the warning message "ADJUSTMENT OF WHITE BALANCE" is displayed on the monitor 40. Namely, by displaying the warning message "ADJUSTMENT OF WHITE BALANCE" on the monitor 40, it is announced that the white-balance should be readjusted due to the total lit-time of the lamp 20' reaching 50 hours.

At step 124, the variable data N is incremented by "1". Then, at step 125, it is determined whether the readjustment of the white-balance is completed. Note, the readjustment of the white-balance is performed in substantially the same manner as the above-mentioned initial adjustment of the white-balance. When the readjustment of the white-balance has not been completed, the control skips step 126 to step 127. On the other hand, if the readjustment of the white-balance has been completed, the control proceeds from step 125 to step 126, in which the white-balance-adjustment-demand flag WF is made to be "0", whereby the warning message "ADJUSTMENT OF WHITE BALANCE" deleted from the monitor 40. After the white-balance-adjustment-demand flag WF is made to be "0", the control proceeds to step 127.

At step 127, the following calculations are executed:

SD←SD−1

AD←AD+1

Namely, the subtraction-data SD is decremented by "1", and the addition-data AD is incremented by "1".

Note, similar to steps 112 and 113 (the flag F3), steps 118 and 119 (the flag F4) are provided to avoid the decrementing of the subtraction-data SD and the incrementing of the addition-data AD during a first execution of the routine subsequent to the turning-ON of the lamp ON/OFF switch 48, whereby the counting of the subtraction-data SD and the addition-data AD can be correctly performed.

Then, at step 128, it is determined whether the lamp ON/OFF switch 38 is turned OFF. When the lamp ON/OFF switch 48 is ON, the routine once ends. Thereafter, the routine comprising steps 101 to 128 is repeated at the regular intervals of one second as long as the lamp ON/OFF switch 48 is ON.

At step 128, if it is confirmed that the lamp ON/OFF switch 48 is turned OFF, the control proceeds from step 128 to step 119, in which the most recent data SD, AD and N and the most recent states of the flags LF and WF are stored in the non-volatile memory 50C. Then, at step 130, the flag F2 is made to be "0", and the flag F4 is made to be "0". Thereafter, although the routine is repeatedly executed at the regular intervals of one second, there is no progress as long as the lamp ON/OFF switch 48 is OFF. Of course, when the power ON/OFF switch 46 is turned OFF, the execution of the routine is stopped.

At step 105, when the lamp-exchanging signal is high, i.e. when an exchange of the lamp 20 with the new lamp 20' is not detected, the control proceeds from step 104 to step 131 (FIG. 10), in which the flag F2 is made to be "1", and then the control jumps to step 118. Of course, in this case, at step 104, the last data SD, AD and N and the last states of the flags LF and WF are read from the non-volatile memory 50C, and are then written in the RAM 30C of the system control circuit 30.

As is apparent from the foregoing, according to the present invention, not only is a remaining life span of the lamp (20/20') properly calculated without using a conventional life span meter with a mercury column that may result in environmental pollution on disposal, but also it is possible to timely and surely announce a point when the lamp (20/20') should be exchanged with a new lamp (20'/20") and a point when a white-balance should be readjusted.

Finally, it will be understood by those skilled in the art that the foregoing description is of preferred embodiments of the life span meter system, and that various changes and modifications may be made to the present invention without departing from the spirit and scope thereof.

The present disclosure relates to subject matters contained in Japanese Patent Application No. 10-90815 (filed on Mar. 19, 1998) which is expressly incorporated herein, by reference, in its entirety.

What is claimed is:

1. A life span meter system for a light source used in an electronic endoscope, comprising:

a counter that numerically determines a lit-time of said light source as a numerical lit-time data when said light source is turned ON;

a memory that stores said numerical lit-time data as a total numerical lit-time data of said lit-time of said light source when said light source is turned OFF;

a determiner that determines whether said total numerical lit-time data reaches a numerical life span data numerically determined from an expected life span of said light source;

an indicator that indicates said light source should be exchanged with a new light source when it is determined by said determiner that said total numerical lit-time data exceeds said numerical life span data; and a detector that detects an exchange of said light source with said new light source, said detector comprising a light source exchanging signal generating circuit incorporated in a light source mounting mechanism in which said light source is detachably and exchangeably mounted, said light source exchanging signal generating circuit being configured so as to output a light source exchanging signal, indicating that said exchange of said light source with a new light source has been performed, when a mounting of said new light source in said light source mounting mechanism is completed and when said electronic endoscope is electrically energized, wherein said numerical life-span data is numerically determined from said expected life span of said light source when said exchange of said light source with said new light source is detected by said detector.

2. A life span meter system as set forth in claim 1, wherein said counter comprises a subtraction-counter initially setting said numerical life span data to an initial value, and subtracting said numerical lit-time data from said initial value.

3. A life span meter system as set forth in claim 2, wherein said initial value of said subtraction-counter, from which said numerical lit-time data is subtracted, is stored in said memory.

4. A life span meter system as set forth in claim 3, wherein said determiner determines whether said initial value of said subtraction-counter, from which said numerical lit-time data is subtracted, is less than zero, and said indicator indicates that said light source should be exchanged with said new light source when it is determined by said determiner that said initial value of said subtraction-counter is less than zero.

5. A life span meter system as set forth in claim 1, wherein said light-source-exchanging-signal generating circuit is formed as a switching circuit including a voltage-applied electric line, a grounded electric line, and a movable electric contact which is arranged such that an electrical contact is established between said voltage-applied electric line and said grounded electric line when said mounting of said new light source in said light-source-mounting is completed, resulting in said outputting of said light-source-exchanging signal.

6. A life span meter system as set forth in claim 5, wherein said light-source-mounting mechanism includes a movable light-source mounting plate for mounting said light-source, a movable switching plate member carrying said electric contact, associated with said light-source-mounting plate such that said switching plate member is moved in accordance with a movement of said light-source-mounting plate, and a locking unit for locking said switching plate member at a predetermined position during a movement of said switching plate member by said light-source mounting plate, said electrical contact being established between said voltage-applied electric line and said grounded electric line when said switching plate member is positioned and locked at said predetermined position by said locking unit.

7. A life span meter system as set forth in claim 6, wherein said switching plate member is provided with a spring unit which is arranged so as to be subjected to a compression when said switching plate member is positioned and locked at said predetermined position by said locking unit, said switching plate member being moved from said predetermined position due to said compression of said spring unit so that an electrical disconnection is established between said voltage-applied electric line and said grounded electric line when being unlocked by said locking unit.

8. A life span meter system as set forth in claim 1, further comprising a second indicator that indicates an initial adjustment of a white-balance should be performed when said exchange of said light source with said new light source is detected by said detector.

9. A life span meter system as set forth in claim 1, further comprising a second indicator that indicates a readjustment of a white-balance should be performed when said numerical lit-time data reaches a multiple of a pre-set numerical data over a period of said numerical life span data.

10. The life span meter system for a light source according to claim 1, said light source exchanging signal generating circuit being configured so as to output a light source exchanging signal indicating that said exchange of the light source with the new light source has been performed, when a mounting of said new light source in said light source mounting mechanism is completed, when said electronic endoscope is electrically energized, and when a light switch is electrically energized.

* * * * *